(12) United States Patent
Compton et al.

(10) Patent No.: US 11,666,362 B2
(45) Date of Patent: *Jun. 6, 2023

(54) BONE STRUCTURE COUPLING SYSTEMS AND METHODS OF USE

(71) Applicants: Robert A. Compton, Bixby, OK (US); Mark Billy Willits, Kellyville, OK (US)

(72) Inventors: Robert A. Compton, Bixby, OK (US); Mark Billy Willits, Kellyville, OK (US)

(73) Assignee: Med Device IP, LLC, Bixby, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 16/289,922

(22) Filed: Mar. 1, 2019

(65) Prior Publication Data

US 2020/0060733 A1   Feb. 27, 2020

Related U.S. Application Data

(63) Continuation of application No. 15/793,105, filed on Oct. 25, 2017, now Pat. No. 10,219,841.

(51) Int. Cl.
*A61B 17/88* (2006.01)
*A61B 17/70* (2006.01)
(Continued)

(52) U.S. Cl.
CPC ...... *A61B 17/7055* (2013.01); *A61B 17/1615* (2013.01); *A61B 17/1659* (2013.01);
(Continued)

(58) Field of Classification Search
CPC ............ A61B 17/7055; A61B 17/1615; A61B 17/1659; A61B 17/1671; A61B 17/1757; A61F 2/30771; A61F 2/4455; A61F 2/447; A61F 2/4611; A61F 2002/2835; A61F 2002/30153; A61F 2002/30784;
(Continued)

(56) References Cited

U.S. PATENT DOCUMENTS

| | | | | |
|---|---|---|---|---|
| 4,349,921 A | * | 9/1982 | Kuntz | A61F 2/4425 |
| | | | | 623/17.16 |
| 4,834,757 A | * | 5/1989 | Brantigan | A61B 17/1604 |
| | | | | 623/17.11 |

(Continued)

FOREIGN PATENT DOCUMENTS

EP   3315085 A1 * 5/2018 ......... A61B 17/7055

*Primary Examiner* — Eduardo C Robert
*Assistant Examiner* — David C Comstock
(74) *Attorney, Agent, or Firm* — Lexigent LLC

(57) ABSTRACT

Bone structure coupling devices and methods are provided herein. An example method includes positioning a tubular retraction guide body into a patient, the tubular retraction guide body having two prongs that are positioned in a joint between two adjacent bone structures, creating a hemispherical groove on each of the two adjacent bone structures using a drill bit passed through the tubular retraction guide body, incising out the hemispherical grooves with a broach passed through the tubular retraction guide body, and inserting a graft body having a generally rectangular cross sectional area into the angular grooves to couple the two adjacent bone structures together.

16 Claims, 10 Drawing Sheets

(51) Int. Cl.
*A61F 2/44* (2006.01)
*A61B 17/16* (2006.01)
*A61F 2/30* (2006.01)
*A61B 17/17* (2006.01)
*A61F 2/46* (2006.01)
*A61F 2/28* (2006.01)

(52) U.S. Cl.
CPC ...... *A61B 17/1671* (2013.01); *A61B 17/1757* (2013.01); *A61F 2/30771* (2013.01); *A61F 2/447* (2013.01); *A61F 2/4455* (2013.01); *A61F 2/4611* (2013.01); *A61F 2002/2835* (2013.01); *A61F 2002/30153* (2013.01); *A61F 2002/30784* (2013.01); *A61F 2002/30795* (2013.01); *A61F 2002/30904* (2013.01); *A61F 2002/30995* (2013.01); *A61F 2002/4681* (2013.01)

(58) Field of Classification Search
CPC .. A61F 2002/30795; A61F 2002/30904; A61F 2002/30995; A61F 2002/4681
USPC ........ 606/246, 279, 80, 84, 85, 90, 99, 86 A
See application file for complete search history.

(56) References Cited

U.S. PATENT DOCUMENTS

| | | | |
|---|---|---|---|
| 5,425,772 A * | 6/1995 | Brantigan | A61F 2/447 623/17.11 |
| 5,554,191 A * | 9/1996 | Lahille | A61B 17/1757 623/17.11 |
| 6,200,322 B1 * | 3/2001 | Branch | A61B 17/1757 606/96 |
| 7,648,509 B2 | 1/2010 | Stark | |
| 8,808,377 B2 | 8/2014 | Donner | |
| 9,119,732 B2 | 9/2015 | Schifano et al. | |
| 9,186,155 B2 | 11/2015 | Katzman et al. | |
| 9,241,798 B2 | 1/2016 | Petersen | |
| 9,375,243 B1 | 6/2016 | Vestgaarden | |
| 9,421,109 B2 | 8/2016 | Donner et al. | |
| 9,451,986 B2 | 9/2016 | Stoffman et al. | |
| 9,662,158 B2 | 5/2017 | Reiley | |
| 10,357,368 B2 | 7/2019 | Aksu | |
| D905,232 S | 12/2020 | Schifano et al. | |
| 10,993,757 B2 | 5/2021 | Schifano et al. | |
| 2002/0077641 A1 * | 6/2002 | Michelson | A61F 2/4611 606/167 |
| 2003/0083664 A1 * | 5/2003 | Rogers | A61B 17/1671 606/79 |
| 2007/0027544 A1 * | 2/2007 | McCord | A61F 2/447 623/17.11 |
| 2010/0268228 A1 | 10/2010 | Petersen | |
| 2011/0184518 A1 | 7/2011 | Trieu | |
| 2012/0004660 A1 * | 1/2012 | Grooms | A61F 2/4644 606/79 |
| 2012/0095560 A1 | 4/2012 | Donner | |
| 2012/0296428 A1 | 11/2012 | Donner | |
| 2013/0211526 A1 * | 8/2013 | Alheidt | A61F 2/442 623/17.16 |
| 2013/0238093 A1 * | 9/2013 | Mauldin | A61F 2/28 623/16.11 |
| 2013/0304070 A1 * | 11/2013 | Nelson | A61B 18/148 606/85 |
| 2014/0276846 A1 * | 9/2014 | Mauldin | A61B 17/1664 606/80 |
| 2015/0148907 A1 * | 5/2015 | Kleiner | A61F 2/4601 623/17.16 |
| 2016/0310197 A1 | 10/2016 | Black et al. | |
| 2017/0042696 A1 * | 2/2017 | Larsson | A61F 2/4455 |

* cited by examiner

BONE STRUCTURE COUPLING SYSTEMS AND METHODS OF USE

CROSS REFERENCE TO RELATED APPLICATIONS

This application is a continuation of and claims the benefit and priority of U.S. application Ser. No. 15/793,105, filed on Oct. 25, 2017, titled "BONE STRUCTURE COUPLING SYSTEMS AND METHODS OF USE" which is hereby incorporated by reference herein in its entirety, including all references and appendices cited therein, for all purposes.

FIELD OF THE INVENTION

The present technology pertains to systems and methods for bone structure coupling or connecting, and more specifically, but not by way of limitation, to systems and methods that couple or connect two or more adjacent bone structures, such as adjacent bone structures in a sacroiliac joint.

SUMMARY

Various embodiments of the present disclosure are directed to a device, comprising: a graft body comprising a generally rectangular cross sectional area, a first end, and a second end, the graft body comprising a plurality of rows of teeth; a head extending from the first end of the graft body; and an adaptor extending from the second end, the adaptor being spaced apart from a last of the plurality of rows of teeth to form an inserter device groove, the adaptor terminating with an inserter device interface, wherein the inserter device interface is configured to mate with an adaptor interface of an inserter device, wherein the plurality of rows of teeth are oriented so as to prevent migration or ejection of the graft body when inserted into a pilot hole created in adjacent bone structures.

Various embodiments of the present disclosure are directed to a method, comprising: positioning a tubular retraction guide body into a patient, the tubular retraction guide body having two prongs that are positioned in a joint between two adjacent bone structures; creating a hemispherical groove on each of the two adjacent bone structures using a drill bit passed through the tubular retraction guide body; incising the hemispherical grooves with a broach passed through the tubular retraction guide body, the broach transforming the hemispherical grooves into angular grooves; and inserting a graft body having a generally rectangular cross sectional area into the angular grooves to couple the two adjacent bone structures together.

Various embodiments of the present disclosure are directed to a method, comprising: positioning a tubular retraction guide body into a patient between two adjacent bone structures separated from one another; creating a pilot hole using a drill bit passed through the tubular retraction guide body, the pilot hole creating a hemispherical groove on outer surfaces of each of the two adjacent bone structures in a single pass; inserting a graft body having a generally rectangular cross sectional area through the tubular retraction guide and into the pilot hole; and driving the graft body into the pilot hole to incise out the hemispherical grooves into angular grooves by rows of cutting teeth on the graft body, wherein the graft body secures together the two adjacent bone structures.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Generally described, the present technology is directed to devices and methods of use that can be utilized to couple together adjacent bone structures. For example, the devices disclosed herein can be utilized to fuse or connect adjacent bone structures in a sacroiliac joint. While many examples provided herein will be discussed with reference to the sacroiliac joint for purposes of brevity and clarity, one of ordinary skill in the art will appreciate that the devices and methods disclosed herein can be utilized for coupling adjacent bone structures in any location within a patient. Also, it will be understood that the term 'coupled' as used herein should be understood to include connection, linkage, fusing, or other similar terminology, as would be appreciated by one of ordinary skill in the art. Generally, the concept of coupling described herein is related to maintaining two or more bone structures in mating or close, but spaced apart relationship with one another. For example, a mating and/or spaced but close relationship exists between the ilium and sacrum, known as the sacroiliac joint. The coupling of the ilium and sacrum is a function of the structure of both bones and how they interface. This relationship is maintained by a vast network of ligaments and muscles that prevent excessive separation between the ilium and sacrum. Excessive separation can occur for a one or more of a myriad of etiologies. The devices and methods of the present disclosure advantageously restore a proper and/or desired orientation between the iliac and sacrum by fitting one or more grafts inside the sacroiliac joint that effectively couple the bone structures of the ilium and sacrum. Grafts disclosed herein advantageously resist natural flexion or movement between the iliac and sacrum while maintaining a desired orientation between the iliac and sacrum when the iliac and sacrum are in a neutral position.

These and other advantages of the present disclosure will be described in greater detail below with reference to FIGS. 1-16.

Figure 15:
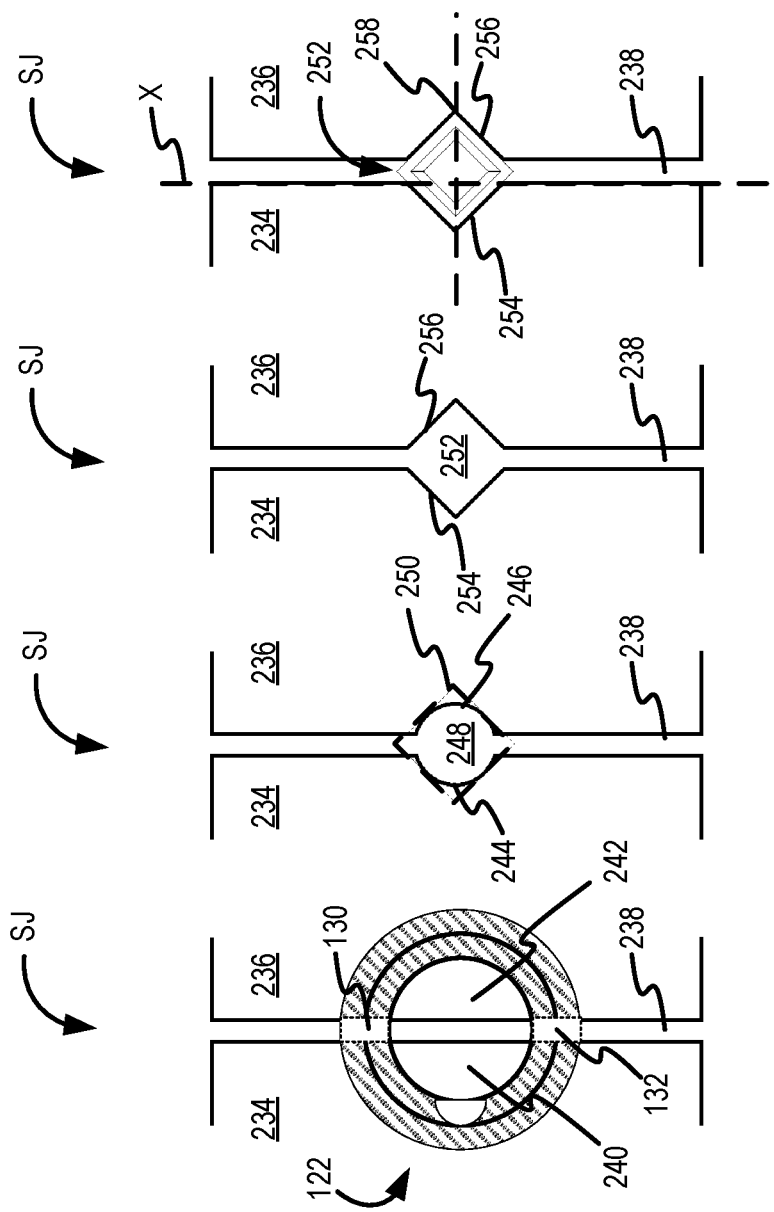
FIG. 15 is a diagrammatic view of the creation a rectangular pilot hole that receives the graft of FIGS. 10 and 11, in accordance with the present disclosure.

FIG. 1A is a perspective view of an example finder device 100. The finder device 100 comprises a tubular finder body 102 having a first end 104 and a second end 106. The tubular finder body 102 comprises a pathway 110 extending from an opening 108 in the first end 104 to an opening (not shown) in the second end 106. The pathway 110, in some embodiments, is a cylindrical pathway. The cylindrical pathway receives a guide rod (not shown) that generally locates a sacroiliac joint (SJ) in a patient. An example representation of a SJ is illustrated in FIG. 15, for example. The guide rod is positioned inside the SJ, and the finder device 100 is passed over the guide rod.

Figure 1:
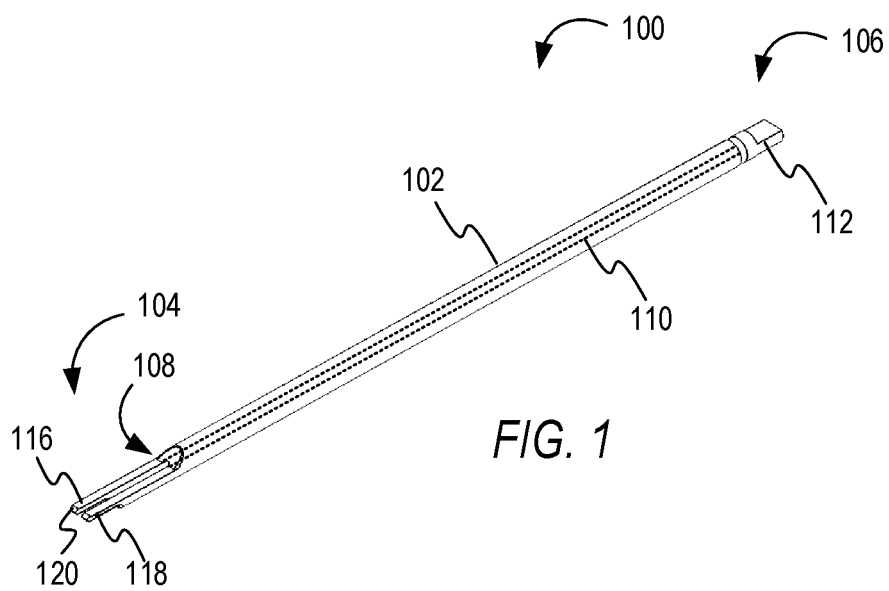
FIG. 1 is a perspective view of a joint finder device constructed in accordance with the present disclosure.
Figure 2A:
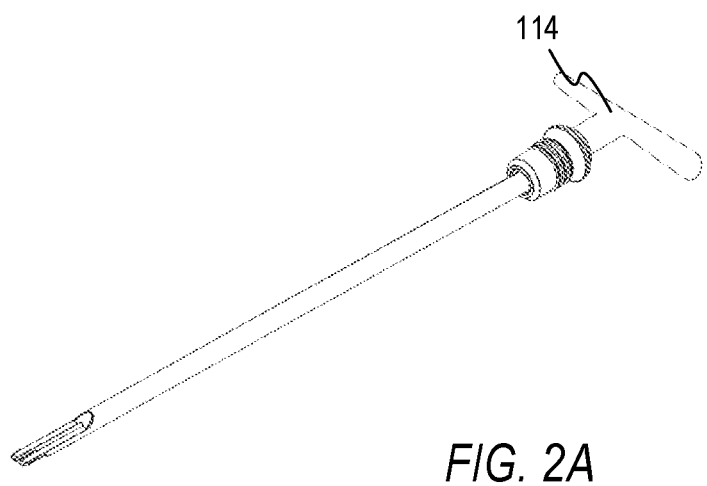
FIG. 2A is a perspective view of the joint finder device having a T-handle coupled thereto.

The second end 106 of the finder device 100 comprises an interface 112 that is configured to mate with a T-shaped handle 114, as illustrated in FIG. 2A.

The first end 104 of the finder device 100 comprises finder arms 116 and 118. The finder arms 116 and 118 are positioned inside the SJ.

If required, the T-handle 114 functions as a means to drive the finder arms 116 and 118 into the SJ, and also to force the finder arms 116 and 118 through any tissues that may exist between the finder arms 116 and 118 the SJ, such as ligaments or muscles that overlay the bone structures. In one or more embodiments, the ends of the finder arms 116 and 118, such as end 120 are chiseled to allow the finder arms 116 and 118 to dissect through tissue.

Figure 2B:
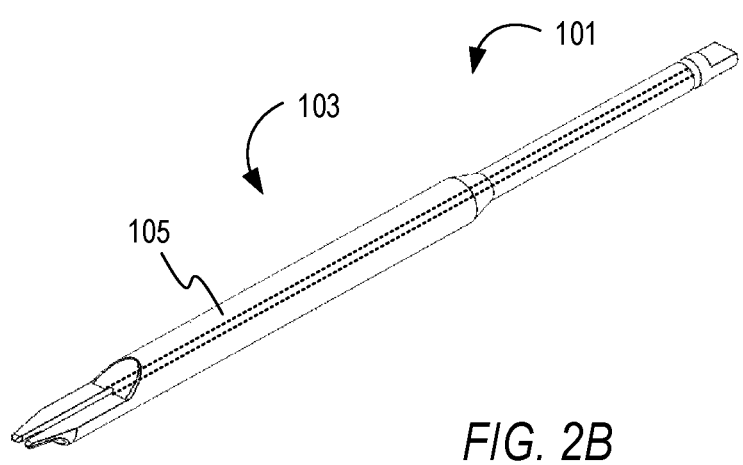
FIG. 2B is a perspective view of another joint finder device.

FIG. 2B is a perspective view of another example finder device 101. This finder device 101 is similar to the finder device 101 of FIGS. 1A and 2A with the exception that the tubular finder body 103 has an enlarged diameter section 105 that is more closely sized to an internal diameter of a retraction guide (see FIGS. 3 and 4).

Figure 3:
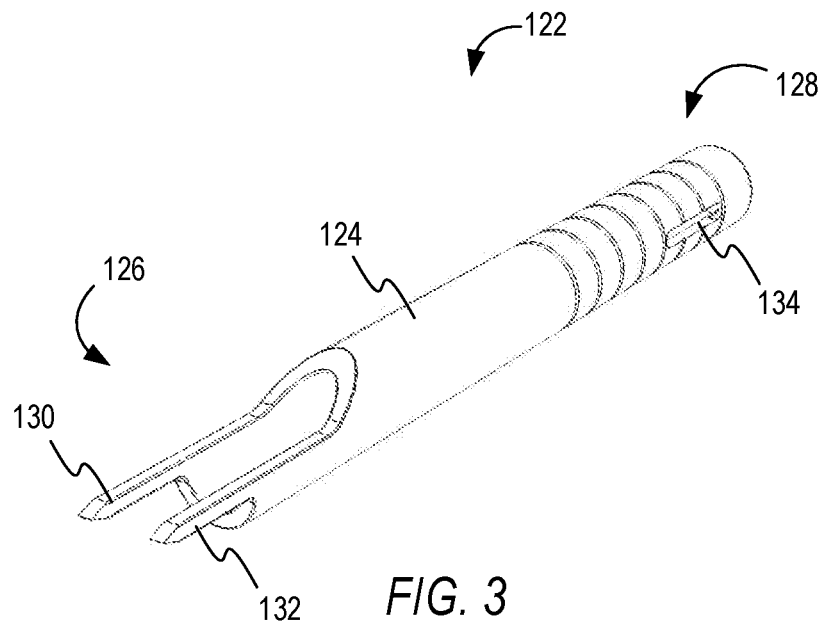
FIG. 3 is a perspective view of a retraction guide constructed in accordance with the present disclosure.

FIG. 3 is a perspective view of an example retraction guide 122 of the present disclosure. The retraction guide 122 comprises a retraction guide body 124 that is hollow. The inner diameter of the retraction guide body 124 is sized to allow for the retraction guide 122 to be slid over the finder device 100 (when the T-handle 114) is not coupled to the finder device 100.

Generally, the retraction guide body 124 comprises a first end 126 and a second end 128. The first end comprises retraction body arms 130 and 132. When the retraction guide 122 is slid over the finder device 100, the retraction body arms 130 and 132 are oriented in parallel with the finder arms 116 and 118 of the finder device 100. The retraction body arms 130 and 132 are then driven into the SJ.

Figure 4:
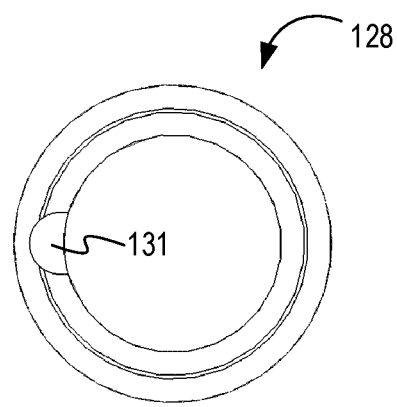
FIG. 4 is a rear plan view of the retraction guide of FIG. 3.

In one or more embodiments, as in FIG. 4, the second end 128 comprises a notch 131. The notch 131 provides a groove fabricated into a second end surface. The notch 131 is used as a guide for receiving a detent (e.g., protrusion) of various other instruments that are guided through the retraction guide 122, as will be discussed infra. A portion of the notch 131 is visible through a window 134 created in a sidewall of the retraction guide body 124. The window 134 provides a view of a position of an inserted tool. To be sure, each of the tools/devices disclosed herein that are configured to be slidably inserted into the retraction guide 122 can comprise a detent/protrusion as disclosed below.

The retraction guide 122 stays in place inside the SJ while subsequent devices and methods are utilized in cooperation with the retraction guide body 122.

Figure 5:
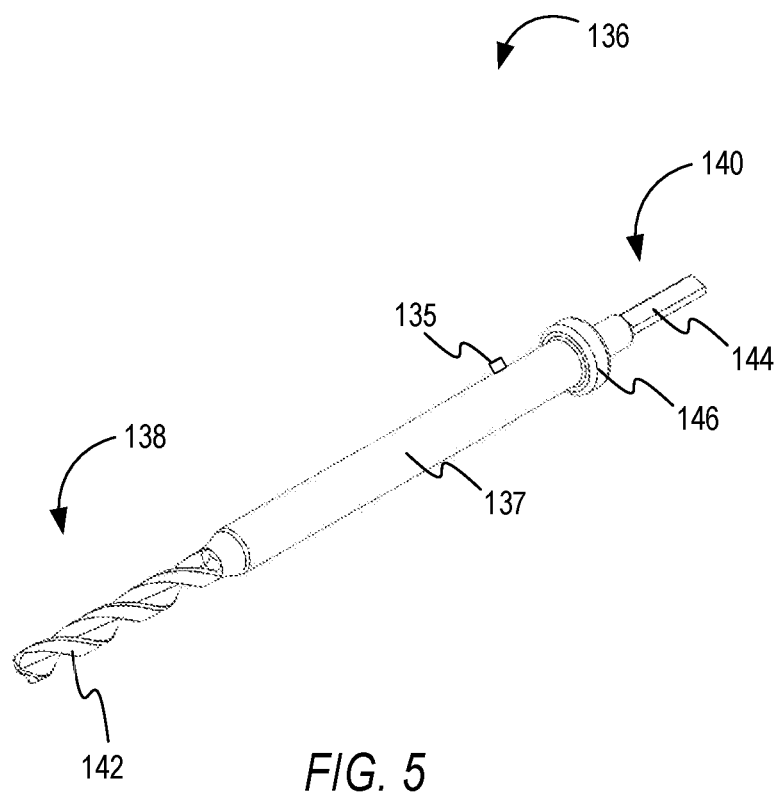
FIG. 5 is a perspective view of a drill bit constructed in accordance with the present disclosure.

FIG. 5 is a perspective view of an example drill bit 136. The drill bit 136 comprises a drill bit shank 137. The drill bit shank 137 comprises a first end 138 and a second end 140. A bit 142 is disposed on the first end 138 and an interface 144 is disposed on the second end 140. The interface 144 is configured to engage with a drill. In some embodiments, the tip (e.g., cutting edge) of the drill bit 136 is configured to cut into the respective bone structures, while the remaining flute and web of the bit 142 create a shaft of the pilot hole.

In some embodiments, the second end 140 comprises a collar 146. The collar 146 functions as a stop when the drill bit 136 is placed into the retraction guide body 124. When the drill bit 136 is passed through the retraction guide body 124, the collar 146 will stop when impacting the second end surface 133 of the second end 128 of the retraction guide body 124. A protrusion 135 can be disposed on the drill bit shank 137.

The bit 142 is shaped to create to bore a substantially cylindrical pilot hole in the SJ. The creation of an example cylindrical pilot hole is illustrated with respect to FIG. 15, which is described in greater detail infra.

Figure 6:
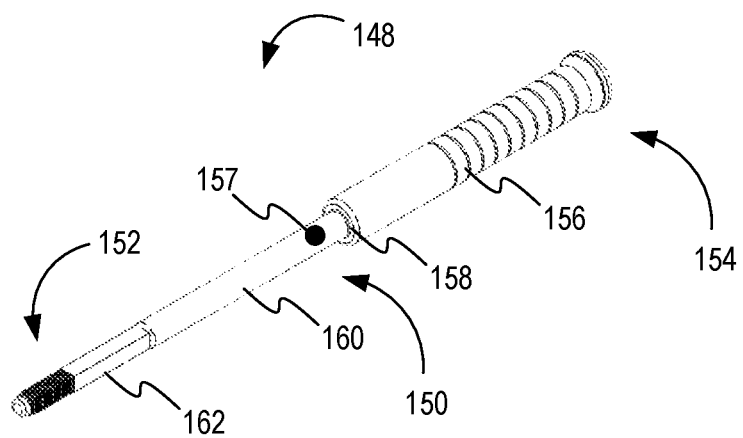
FIG. 6 is a perspective view of an example broach device constructed in accordance with the present disclosure.
Figure 7:
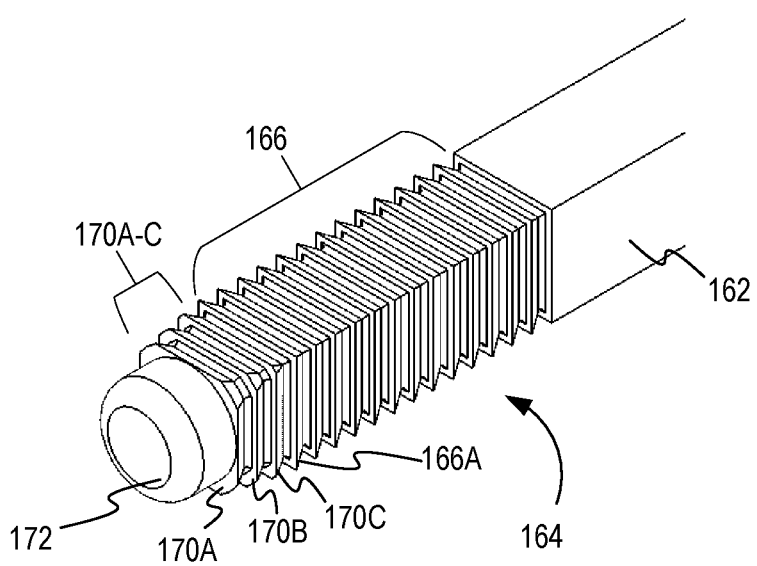
FIG. 7 is a close up, perspective view of a incising member of the example broach device.
Figure 8:
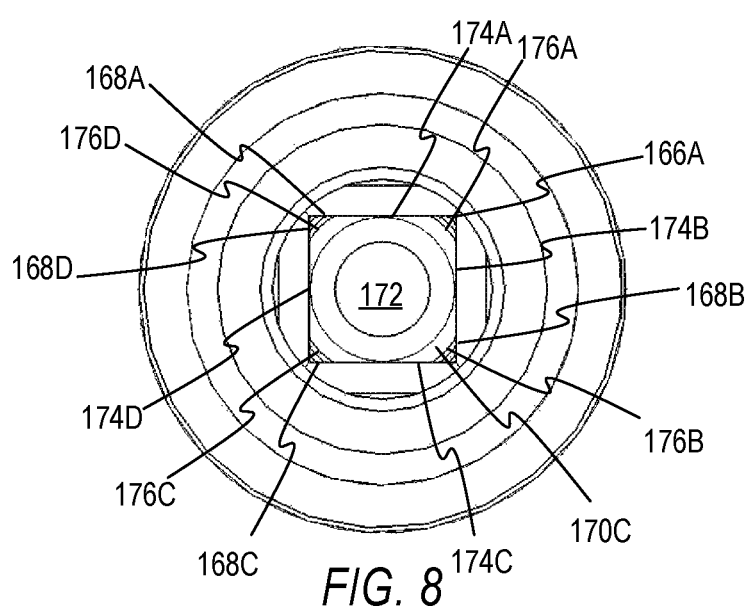
FIG. 8 is a front plan view of the incising member of the example broach device of FIGS. 6 and 7.

FIGS. 6-8 collectively illustrate an example broach device 148, for use in accordance with embodiments of the present disclosure. In various embodiments, the broach device 148 generally comprises a broach body 150 with a first end 152 and a second end 154. The second end 154 of the broach body 150 comprises a handle 156. The handle 156 forms a collar 158 at a terminal end thereof. As with other tools, the collar 158 limits the translation of the broach device 148 when inserted into the retraction guide 122 (see FIGS. 3 and 4).

In more detail, the broach body 150 comprises a substantially cylindrical portion 160, which transitions into a substantially rectangular portion 162. An incising member 164 is disposed at the end of the substantially rectangular portion 162. In some embodiments, a portion of the incising member 164 has a generally rectangular cross sectional area. The cylindrical portion 160 is a generally cylindrical head that is insertable within the spaced-apart aperture formed by the drill bit.

While a substantially rectangular portion 162 has been disclosed, any other geometrical configuration can also likewise be utilized. In general, the shape of the substantially rectangular portion 162 and incising member 164 correspond to a size and shape of a graft that is to be placed into the SJ, as will be discussed in greater detail below.

The broach body 150 comprises a protrusion 157 that is configured to fit within the notch 131 of the retraction guide 122 (see FIGS. 3 and 4). When the broach body 150 is inserted into the retraction guide 122, the protrusion 157 travels within the notch 131 to ensure proper alignment of the incising member 164. A proper orientation of the incising member 164 will ensure that angular grooves are created in adjacent bone structures of the SJ.

FIG. 7 is a close-up perspective view of the incising member 164 comprises a set of cutting teeth 166 that are substantially similar in shape and size relative to one another. Each of the set of cutting teeth 166 has a generally rectangular outer peripheral geometry (see FIG. 8). For example, cutting tooth 166A comprises four sides 168A-D. Each row behind the cutting tooth 166A is shaped similarly to that of cutting tooth 166A. Rows 170A-C disposed in front of cutting tooth 166A provide a transition between a cylindrical broach tip 172 and the set of cutting teeth 166 (e.g., rectangular, circumferential cutting teeth).

In general, the cylindrical broach tip 172 is sized to fit into the pilot hole created by the drill bit 136 of FIG. 5. Cutting tooth 170A is disposed immediately behind the cylindrical broach tip 172 comprises four linear edges 174A-D. In between adjacent ones of the four linear edges 174A-D are arcuate edges 176A-D (e.g., arcuate chamfer). For example, arcuate edge 176A is disposed between linear edge 174A and linear edge 174B. A size of arcuate edges decreases from cutting tooth 170A to cutting tooth 170C. This allows for the incising member 164 to transitionally incise out the cylindrical pilot hole created by the drill bit 136 to create a substantially rectangular pilot hole. This process is diagrammatically illustrated in FIG. 15, which is described in greater detail below.

In sum, the each of the initial set of rows 170A-C has a different outer-peripheral shape based on its distance from the broach tip 172. The closer a cutting tooth is to the broach tip 172, the larger the arcuate edges are for that cutting tooth.

Figure 9:
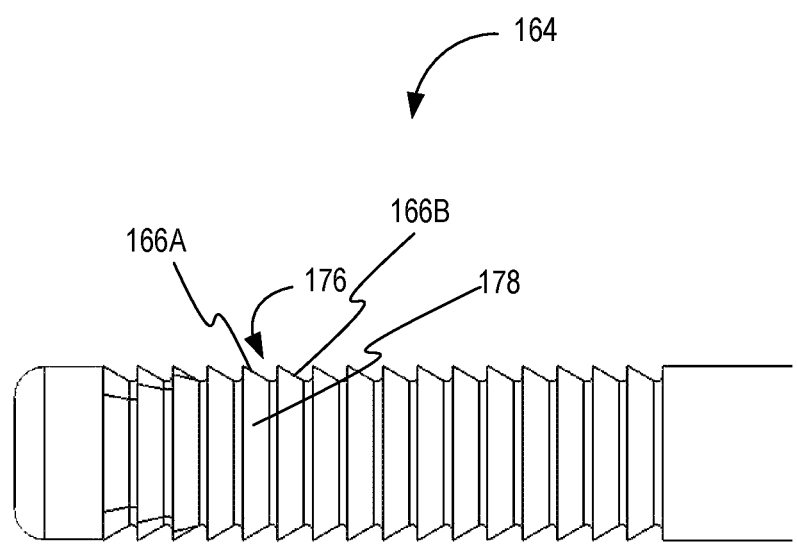
FIG. 9 is a side elevation view of the incising member of the example broach device of FIGS. 6-8.

As best illustrated in FIG. 9, adjacent cutting teeth are spaced apart from one another to create grooves, such as groove 176 that receives bone fragments when the incising member 164 is driven into the cylindrical pilot hole. These grooves are effectively similar to flutes of a drill bit with the exception that the grooves are not continuous, but individual. In some embodiments, a forwardly adjacent cutting tooth, such as cutting tooth 166A has a tapered and contoured body portion 178 that extends toward cutting tooth 166B. This tapered and contoured body portion 178 creates a hook-shape for the groove 176.

Figure 10:
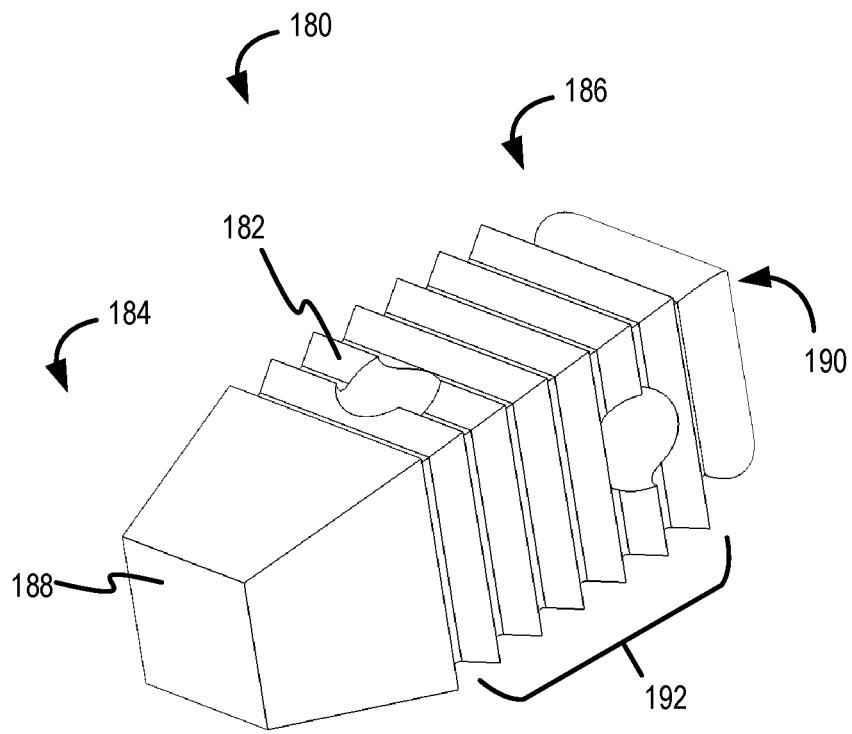
FIGS. 10 and 11 are perspective views of an example graft device constructed in accordance with the present disclosure.
Figure 11:
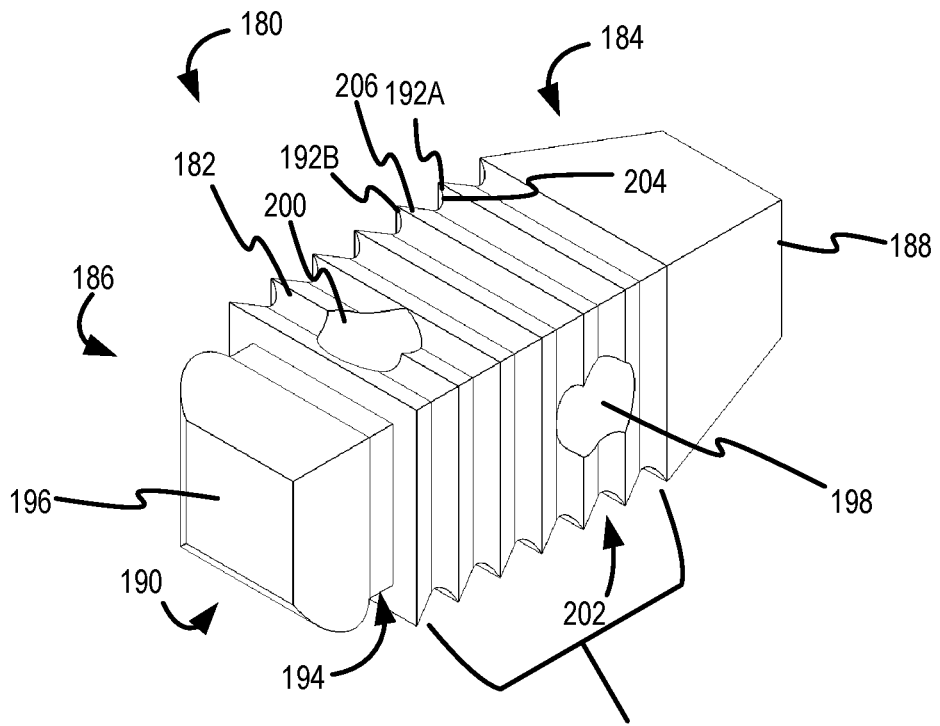

Once the substantially rectangular pilot hole has been created by the broach device 148, the substantially rectangular pilot hole is ready to receive a graft, such as the graft 180 of FIGS. 10 and 11. Generally, the graft 180 comprises a graft body 182 with a first end 184 and a second end 186.

In some embodiments, the graft body 182 has a substantially rectangular shape that matches the substantially rectangular pilot hole created as described above. In various embodiments, the first end 184 of the graft body 182 has a head 188 that comprises a blunt, tapered polygonal sided head.

In some embodiments, an adaptor 190 extends from the second end 186. The adaptor 190 is spaced apart from a last of the plurality of rows of teeth 192 to form an inserter device groove 194.

The adaptor 190 terminates with an inserter device interface 196. In some embodiments, the inserter device interface 196 is configured to mate with an adaptor interface of an inserter device, which is described infra. In some embodiments, the plurality of rows of teeth 192 are oriented so as to prevent migration or ejection of the graft body 182 when inserted into the rectangular pilot hole described above.

In one or more embodiments, the graft body 182 comprises apertures such as aperture 198 that provide a pathway for the growth of bone when the graft 180 has been inserted into the substantially rectangular pilot hole. In some embodiments, a second aperture 200 is fabricated in a direction that is substantially orthogonal to the aperture 198, allowing for additional directional bone growth and improved securement of the graft 180 over time.

The graft 180 is inserted head first into the substantially rectangular pilot hole. Also, the plurality of rows of teeth 192 are oriented in a direction that is opposite of an orientation/direction of the cutting teeth of the incising member 164 (see FIGS. 6-8). This configuration and orientation of the graft 180 ensures that the plurality of rows of gripping teeth 192 will resist shearing forces (or other forces) that might otherwise cause the graft 180 to back out of the substantially rectangular pilot hole.

In some embodiments, adjacent teeth, such as tooth 192A and 192B are spaced apart to create a hook-shaped groove 202. The hook-shaped groove 202 is formed by an arcuate taper 204 from tooth 192A and linear transition 206 to tooth 192B.

Figure 12:
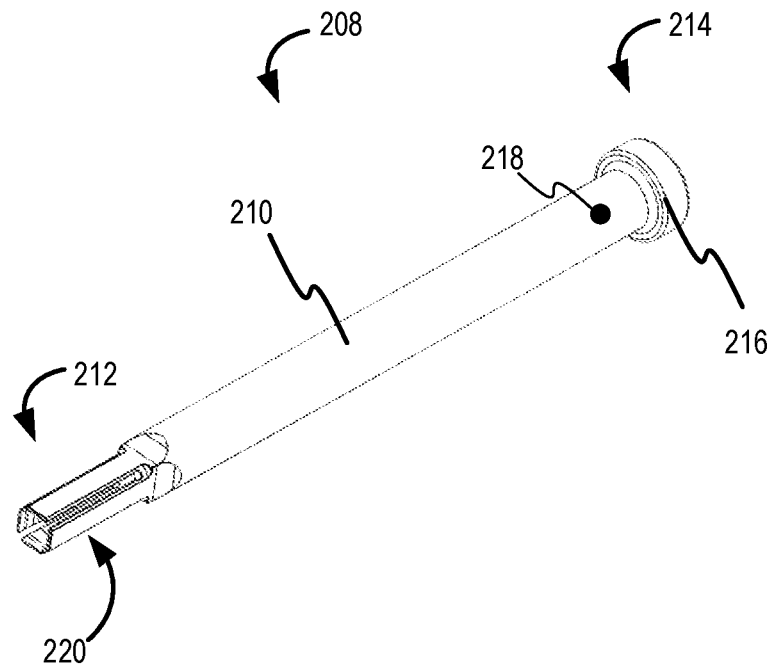
FIG. 12 is a perspective view of an example graft inserter device constructed in accordance with the present disclosure.

FIG. 12 illustrates an example inserter device 208. The inserter device 208 comprises an inserter body 210 with a first end 212 and a second end 214. The second end 214 comprises a collar (e.g., annular stop) 216 and protrusion 218. The collar 216 acts as a stop that limits the translation of the inserter device 208 relative to the retraction guide 122.

When the inserter body 210 is inserted into the retraction guide 122, the protrusion 218 travels within the notch 131 of the retraction guide 122 to ensure proper alignment of the graft 180 (see FIG. 13) relative to the substantially rectangular pilot hole created by the incising member 164 of the broach device 148. The inserter body 210 is sized to be received within the retraction guide 122.

The first end 212 comprises an adaptor interface 220 that releaseably retains the graft 180. The adaptor interface 220, in some embodiments, comprises a plurality of resiliently biased tabs (such as tab 222) that are spaced apart from one another so as to allow for independent movement. The tab 222 has a configuration that is essentially a negative profile of a side of the adaptor 190 of the graft 180.

Figure 13:
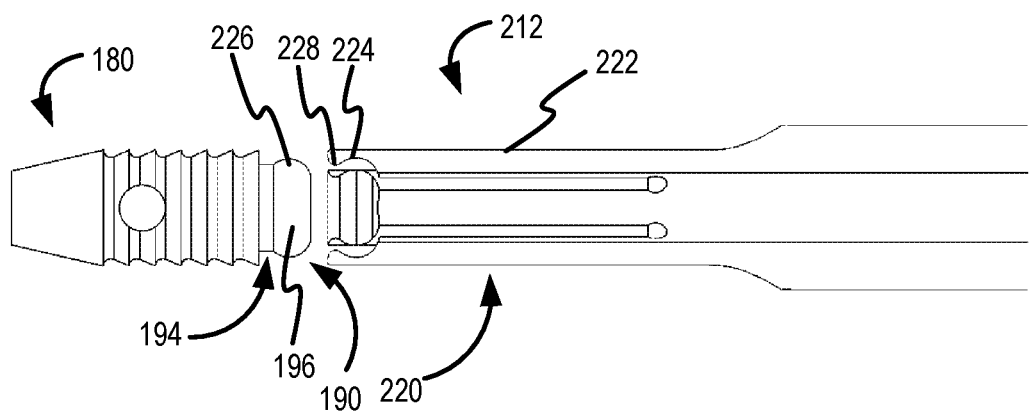
FIG. 13 is a cross sectional and exploded view of a graft in combination with a portion of the example graft inserter device of FIG. 12.

As best illustrated in FIG. 13, in some embodiments, each of the plurality of resiliently biased tabs comprises a groove 224 that receives one of the plurality of arcuate sidewalls (such as arcuate sidewall 226 of the graft's inserter device interface 196 of the adaptor 190. The tab 222 also comprises a detent 228 that engages with the inserter device groove 194 of the graft 180. The adaptor 190 of the graft 180 is snapped or otherwise engaged into a space formed by the plurality of resiliently biased tabs. The plurality of resiliently biased tabs deflect to receive the adaptor 190 and clamp around the adaptor 190 based on the shape of the terminal ends of the plurality of resiliently biased tabs.

Figure 14:
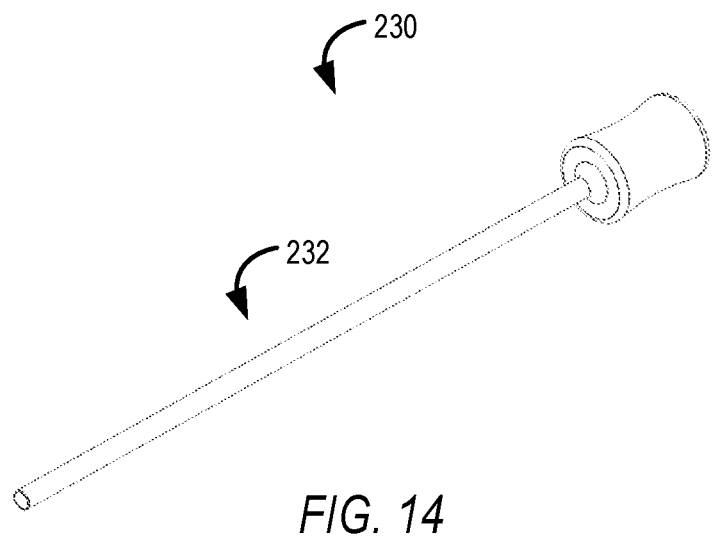
FIG. 14 is a perspective view of an example impactor device constructed in accordance with the present disclosure.

In some embodiments, the inserter body 210 is hollow and provides a pathway that receives an impactor device 230 as illustrated in FIG. 14. FIG. 14 is a perspective view of an example impactor device 230 that can be inserted through a pathway in the inserter body 210. The impactor device 230 includes a shaft 232 with a terminal end that contacts the adaptor 190 of the graft 180. An opposing end of the impactor device 230 can be impacted to drive the graft 180 into the SJ.

FIG. 15 is a diagrammatic representation of a portion of a sacroiliac joint SJ formed between adjacent bone structures 234 and 236, with bone structure 234 being a sacrum and bone structure 236 being an ilium. Again, this technology is adaptable for use in any joint where bone structures are located in proximate but spaced apart-relationship. The present disclosure can also be utilized in instances where adjacent bone structures are contacting one another. In these instances, the finder and retraction guide disclosed above can be inserted between the contacting adjacent bone structures.

The following description presents an example use case and method for securing the bone structures 234 and 236 using the device(s) of FIGS. 1A-14. Thus, FIGS. 1-15 are collectively referred to in the following sections.

In some embodiments, a space 238 exists between the adjacent bone structures 234 and 236. Although not shown, as noted above, the finder device 100 and retraction guide 122 have their respective arms placed into the space 238. For example, the retraction body arms 130 and 132 of the retraction guide 122 are located in the space 238. This allows a pathway of the retraction guide 122 to be position partially over the bone structure 234 and the bone structure 236.

When the drill bit 136 (see FIG. 5) is passed through the retraction guide 122 sections of the bone structures 234 and 236 are drilled out. For example, section 240 and section 242 are drilled out to create hemispherical grooves 244 and 246 at the same time. That is, the drill bit creates both grooves in a single pass.

These hemispherical grooves are produced when the drill bit passes into and/or transversely over the outer facing surfaces of the adjacent bone structures 234 and 236. That is, the view of the SJ in FIG. 15 is a top down view of the adjacent bone structures 234 and 236 where the drill passed downwardly and transversely across the outer facing surfaces of the bone structures to create an aperture 248. In some embodiments, a spaced-apart aperture is created due to the space 238 that exists between the two adjacent bone structures 234 and 236. Again, the drill bit creates a substantially cylindrical pilot hole (e.g., aperture 248). To be sure, when the adjacent bone structures are contacting one another, the pilot hole or aperture created may not have a spaced-apart appearance or configuration. This device is also capable of being used in a solid bone structure as well, where no joint exists.

The dotted line diamond pattern 250 indicates a desired peripheral shape for a rectangular pilot hole that will be created when the spaced-apart aperture 248 is created using the broach device 148 described above.

In more detail, the incising member 164 of the broach device 148 is located on the pilot hole 248 by inserting the cylindrical broach tip 172 into the pilot hole 248. The broach device 148 is driven into the pilot hole 248 causing the incising member 164 to advance downwardly into the pilot hole 248. In some embodiments, the initial rows of teeth (cutting teeth 170A-C) of the incising member 164 begin to convert the pilot hole 248 into a rectangular pilot hole 252. The shape and configuration of the cutting teeth of the incising member 164 provide a transition between the cylindrical broach tip 172 and the cutting teeth 166, which have a rectangular outer peripheral geometry.

The incising member 164 converts the hemispherical grooves 244 and 246 into angular grooves 254 and 256. In some embodiments a vertex of each of the angular grooves 254 and 256 is approximately orthogonal to a surface of a bone structure. For example, vertex 258 is orthogonal to a plane X that is perpendicular to an outer surface of the bone structure 234.

Next, the graft 180 is positioned at the end of an inserter device (such as the one described above) and is guided downwardly into the rectangular pilot hole 252 through translation of the inserter device through the retraction guide. An impactor device can be used to seat and/or drive the graft 180 into the rectangular pilot hole 252. The graft 180 is driven into the rectangular pilot hole 252 in a head-first orientation, which ensures that the plurality of rows of teeth 192 of the graft 180 (see FIGS. 10 and 11) engage with the surfaces of the adjacent bone structures 234 and 236, seating the graft 180 in a secure manner. In general, the plurality of rows of teeth are oriented so as to prevent migration or ejection of the graft body when inserted into a pilot hole created in adjacent bone structures. Over time, the apertures fabricated into the graft body of the graft will begin to fill with bone material and increase the structural integrity of the connection between the adjacent bone structures. That is, installation of the graft 180 will connect, couple, fuse, or otherwise joint together the adjacent bone structures.

In sum, the process described above generally includes a step of positioning a tubular retraction guide body into a patient. The tubular retraction guide body has two prongs or arms that are positioned in a joint between two adjacent bone structures. Next, the method includes creating a hemispherical groove on each of the two adjacent bone structures using a drill bit passed through the tubular retraction guide body. In some embodiments, the method includes incising the hemispherical grooves with a broach passed through the tubular retraction guide body. The broach transforms the hemispherical grooves into angular grooves. Finally, the method includes inserting a graft body having a generally rectangular cross sectional area into the angular grooves to couple the two adjacent bone structures together.

It will be understood that multiple grafts can be installed along the SJ using the methods described above.

Figure 16:
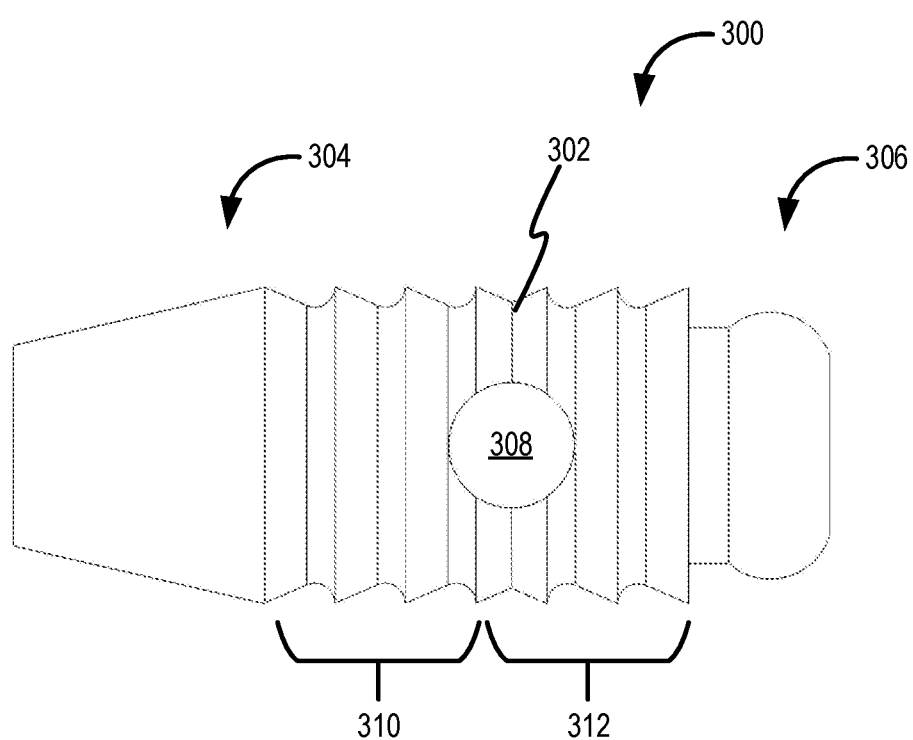
FIG. 16 is a side elevation view of another example graft comprising both cutting teeth and gripping teeth.

FIG. 16 illustrates another example graft 300 that is similar in construction to the graft 180 of FIGS. 10 and 11 with the exception that instead of comprising only gripping teeth; the graft 300 comprises both cutting/incising teeth and gripping teeth.

In some embodiments, a graft body 302 of the graft 300 is provided with a first end 304 and a second end 306. The first end 304 comprises a head with rectangular sides. The second end comprises an inserter interface that cooperates with an inserter device as described above.

In one or more embodiments, the graft body 302 comprises an aperture 308 that provides a pathway for bone growth through the graft body 302. In various embodiments, the graft body comprises a set of cutting teeth 310 adjacent to a set of gripping teeth 312. The set of cutting teeth 310 are oriented in a direction that is opposite of the set of gripping teeth 312. Each of the rows of teeth (whether cutting or gripping) forms a groove with adjacent teeth. These grooves fill with bone material when the graft is inserted into a pilot hole in a joint.

In general the first portion of the plurality of rows of teeth (cutting teeth 310) are configured to remove bone as the graft body is inserted into the pilot hole, the second portion of the plurality of rows of teeth being configured to prevent retraction of the graft body from disengaging from the bone Advantageously, the use of the graft 300 reduces the need to use a broach device, as described above, in order to convert a cylindrical pilot hole into a rectangular pilot hole. In more detail, after a cylindrical pilot hole is created, the graft 300 is inserted into the cylindrical pilot hole and driven into the pilot hole to join adjacent bone structures together. The set of cutting teeth 310 remove bone from the hemispherical grooves of the cylindrical pilot hole, converting the same into a rectangular pilot hole with angular grooves (see FIG. 15). In sum, the graft 300 functions as both a broach and a graft.

Although not shown, the first end 304 and the set of cutting teeth 310 of the graft 300 can be replaced with the cylindrical broach tip 172 and initial cutting teeth 170A-C of the incising member 164 of the broach device 148 (see FIG. 6).

A method for using the graft 300 includes, for example, positioning a tubular retraction guide body into a patient between two adjacent bone structures separated from one another. This can include the use of the finder device, in some embodiments.

Next, the method includes creating a pilot hole using a drill bit passed through the tubular retraction guide body. As noted above, the pilot hole creates a hemispherical groove on outer surfaces of each of the two adjacent bone structures in a single pass.

In some embodiments, the method includes a step of inserting a graft body having a generally rectangular cross sectional area through the tubular retraction guide and into the pilot hole. The method also includes driving the graft body into the pilot hole to incise the hemispherical grooves into angular grooves by rows of cutting teeth on the graft body. To be sure, the graft body secures together the two adjacent bone structures into which the hemispherical grooves were drilled. Again, the rectangular pilot hole is created when cutting teeth disposed in proximity to the head of the graft incise out bone material from the hemispherical grooves.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A system, comprising:
   a graft body comprising a generally rectangular cross sectional area and at least four sidewalls, the graft body comprising a plurality of rows of teeth extending circumferentially and continuously around each of the at least four sidewalls, the plurality of rows of teeth being orthogonal to a direction of insertion of the graft body, the graft body being configured for insertion in a pilot hole, the pilot hole comprising two grooves, each of the two grooves comprising a trench created on an outer surface of opposing bone structures, the graft body extending transversely to the opposing bone structures and situated within the two grooves such that all of the at least four sidewalls of the graft body contact a portion of the opposing bone structures; and
   an inserter device interface that comprises a plurality of arcuate shaped sidewalls that form a protrusion.

2. The system according to claim 1, wherein the graft body comprises one
   or more apertures that provide a pathway for bone growth through the graft body.

3. The system according to claim 1, wherein a first portion of the plurality of rows of teeth are oriented in a first direction and a second portion of the plurality of rows of teeth are oriented in a second direction that is opposite of the first direction, the first portion of the plurality of rows of teeth being configured to remove bone as the graft body is inserted into the pilot hole, the second portion of the plurality of rows of teeth being configured to prevent retraction of the graft body from disengaging from the bone.

4. The system according to claim 1, further comprising an inserter device, wherein the inserter device comprises:
- an inserter device body having a first end and a second end; and
- the first end comprising an adaptor interface, the adaptor interface comprising:
  - a plurality of resiliently biased tabs that are spaced apart from one another so as to allow for independent movement; and
  - wherein each of the plurality of resiliently biased tabs comprises:
    - a groove that receives one of the plurality of arcuate sidewalls of the inserter device interface; and
    - a detent that engages with an inserter device groove of the graft.

5. The system according to claim 4, wherein the second end of the inserter device comprises an annular stop.

6. The system according to claim 5, further comprising a retraction guide that comprises a tubular retraction guide body having an inner sidewall surface, the retraction guide body having two prongs that are positionable in a space between two adjacent bone structures and a drill bit that is configured to create a hemispherical groove on each of the two adjacent bone structures with one pass, wherein the hemispherical grooves form a spaced-apart aperture based on a joint space that exists between the two adjacent bone structures.

7. The system according to claim 6, further comprising a broach comprising:
- a broach body having a first end and a second end;
- a broach tip disposed on the first end of the broach body, the broach tip comprising a generally cylindrical head that is configured to insert within the spaced-apart aperture formed by the drill bit; and
- an incising member comprising a plurality of rectangular, circumferential cutting teeth positioned behind the generally cylindrical head, the plurality of rectangular circumferential cutting teeth incise out the hemispherical grooves to create angular grooves, each with a vertex.

8. The system according to claim 7, wherein the vertex is approximately orthogonal to a surface of a bone structure.

9. The system according to claim 7, wherein the plurality of rectangular, circumferential cutting teeth comprise an initial set of rectangular, circumferential cutting teeth that are proximate the broach tip, each of the initial set comprising four surfaces, wherein each corner of where the four surfaces meet comprise an arcuate chamfered edge.

10. The system according to claim 7, wherein an initial set of the plurality of rectangular, circumferential cutting teeth increases in outer-peripheral area based on a distance from the broach tip.

11. The system according to claim 1, further wherein a head of the graft body is blunt, tapered polygonal sided head.

12. A system, comprising:
- a broach for incising a spaced-apart aperture created by a drill bit, the spaced-apart aperture having hemispherical grooves that are formed into opposing bone structures, the broach incising out the hemispherical grooves to create a pilot hole, the pilot hole comprising two grooves, each of the two grooves comprising a trench created on an outer surface of opposing bone structures; and
- a graft body having at least four sidewalls and a plurality of rows of teeth, the plurality of rows of teeth extending circumferentially and continuously around each of the at least four sidewalls, and being orthogonal to a direction of insertion of the graft body, the graft body comprising an inserter device interface comprising a plurality of arcuate shaped sidewalls that form a protrusion the graft body being configured for insertion in the pilot hole, wherein all of the at least four sidewalls contact a portion of the opposing bone structures and the graft body extends transversely to the opposing bone structures and situated within the two grooves.

13. The system according to claim 12, wherein the graft body comprises one or more apertures that provide a pathway for bone growth through the graft body.

14. The system according to claim 12, wherein a first portion of the plurality of rows of teeth are oriented in a first direction and a second portion of the plurality of rows of teeth are oriented in a second direction that is opposite of the first direction, the first portion of the plurality of rows of teeth being configured to remove bone as the graft body is inserted into the pilot hole, the second portion of the plurality of rows of teeth being configured to prevent retraction of the graft body from disengaging from the bone.

15. The system according to claim 12, wherein a vertex of each of the two opposing v-shaped grooves is approximately orthogonal to a surface of a bone structure.

16. The system according to claim 12, wherein the plurality of rectangular, circumferential cutting teeth comprise an initial set of rectangular, circumferential cutting teeth that are proximate the broach tip, each of the initial set comprising four surfaces, wherein each corner of where the four surfaces meet comprise an arcuate chamfered edge, wherein an initial set of the plurality of rectangular, circumferential cutting teeth increases in outer-peripheral area based on a distance from the broach tip.

* * * * *